United States Patent [19]
Campbell

[11] Patent Number: 5,411,482
[45] Date of Patent: May 2, 1995

[54] VALVE SYSTEM AND METHOD FOR CONTROL OF AN INFUSION PUMP

[75] Inventor: Robert E. Campbell, Chicago, Ill.

[73] Assignee: Infusion Technologies Corporation, Minnetonka, Minn.

[21] Appl. No.: 71,684

[22] Filed: Jun. 3, 1993

Related U.S. Application Data

[63] Continuation-in-part of Ser. No. 969,981, Nov. 2, 1992, Pat. No. 5,232,439, and a continuation-in-part of Ser. No. 970,104, Nov. 2, 1992, Pat. No. 5,342,313.

[51] Int. Cl.⁶ .............................................. A61M 1/00
[52] U.S. Cl. ..................................... 604/153; 604/67
[58] Field of Search ............... 604/67, 132, 153, 141; 128/DIG. 12, DIG. 13

[56] References Cited

U.S. PATENT DOCUMENTS

| | | | |
|---|---|---|---|
| 3,800,794 | 4/1974 | Georgi | 128/DIG. 13 |
| 3,895,741 | 7/1975 | Nugent | 604/67 |
| 4,443,216 | 4/1984 | Chappell | 604/67 |
| 4,563,179 | 1/1986 | Sakai | 604/67 |
| 4,613,327 | 9/1986 | Tegrarian et al. | 128/DIG. 12 |
| 4,650,462 | 3/1987 | DeSatnick et al. | 604/67 |
| 4,714,462 | 12/1987 | DiDomenico | 604/67 |
| 4,822,336 | 4/1989 | DiTraglia | 604/67 |
| 4,874,359 | 10/1989 | White et al. | 604/67 |
| 5,013,303 | 5/1991 | Tamari et al. | 128/DIG. 12 |
| 5,078,682 | 1/1992 | Miki et al. | 604/67 |
| 5,232,439 | 8/1993 | Campbell et al. | 604/28 |

*Primary Examiner*—Paul J. Hirsch
*Attorney, Agent, or Firm*—Jones, Day, Reavis & Pogue

[57] ABSTRACT

A valve system to control administration of fluids from an infusion pump to a patient when the height of the pump relative to the patient is varied. The system comprises a valve which pinches closed the flexible disposable tube that communicates between the pump and the patient unless a minimum pressure is attained in the pump's fluid reservoir. Once the minimum pressure is reached the valve stays open until the pressure in the reservoir drops below a predetermined value which is lower than the minimum "open" pressure. The pressure of the fluid is measured by a sensor pressed against the outside of the reservoir and the valve closes the tube only by externally forcing one external wall against the opposite wall and does not contact the fluid. A method is disclosed for controlling fluid flow of fluids by mechanically closing the tube between the infusion pump and the patient unless a certain minimum pressure is attained in the fluid reservoir and closing the tube again only when the pressure in the reservoir drops to below a certain lower value.

22 Claims, 5 Drawing Sheets

- PATIENT AT OR BELOW PUMP INFUSION RATE
- RAMP-UP; REVERSE FOR RAMP-DOWN

FIG. 12

- PATIENT STANDS UP 4' OVER PUMP
- 400 ml PER HOUR INFUSION RATE

VALVE SYSTEM AND METHOD FOR CONTROL OF AN INFUSION PUMP

This application is a continuation-in-part application of U.S. patent applications Ser. Nos. 969,981, now U.S. Pat. No. 5,232,439, and 970,104, now U.S. Pat. No. 5,342,313, both filed on Nov. 2, 1992.

BACKGROUND OF THE INVENTION

The invention relates generally to infusion pumps and methods of pumping infusion type fluids for intravenous, parenteral, enteral, antibiotic and other medical uses. More specifically, the invention relates to an apparatus and method for safely pumping infusion fluids into a patient when the height of the infusion pump relative to the patient may vary.

Infusion fluids normally are supplied to a patient from a flexible reservoir bag through a long, flexible tube. Sufficient fluid pressure is created by gravity acting on the fluid in the bag and tube to feed the fluid at an acceptable pressure and rate. This was traditionally accomplished in hospital applications by suspending the reservoir bag from a pole. Because the height of the suspended bag relative to the patient varied little regardless of whether the patient was resting in bed or standing, the pressure of the fluid on the patient was not susceptible to significant gravitational, inertial or hydraulic effects which substantial variations in height would create.

As an alternative to passive, gravity-feed infusion, infusion pumps which mechanically induce pressure on the fluid in the bag or other reservoir have been developed. For example, Fletcher et al. U.S. Pat. No. 4,033,479 discloses an apparatus to administer intravenous solutions during space flight by mechanically pressing on the solution-containing bag with a constant pressure. Another example is the device shown in Cherkin U.S. Pat. No. 2,761,445 which squeezes the bag by use of a platform which is moved by a variable speed motor. A more sophisticated, programmable infusion pump is the subject of allowed patent application U.S. Ser. No. 969,981, entitled Method for Pumping Fluid From A Flexible, Variable Geometry Reservoir, filed Nov. 2, 1992. The entire disclosure of U.S. Ser. No. 969,981 is incorporated by reference herein.

These infusion pumps generally only control the pressure of the fluid in the reservoir or the volume of the reservoir and do not address the pressure of the fluid at the point it is received by the patient. Typical infusion tubing can be four feet long or longer and, therefore, will allow pumps to be placed four feet above or below the patient. Moreover, the height of the pump and associated reservoir relative to the patient may vary during use.

If an infusion pump is located above the patient, the fluid will be under substantially more pressure at the point of infusion into the patient than it is in the reservoir. This "free flow" scenario would not be detected by the pumps described above, which have no means to control a greater than desired flow of fluid which may result from such a situation. Indeed, in the case of the Fletcher et al. device, additional mechanically induced pressure is added by the device to whatever pressures are being experienced by the patient as a result of "free flow."

If the pump is located below the patient, the pump will have to overcome substantial back pressure of the column of fluid in the tube. Potentially, a patient in a back pressure situation will lose a significant amount of the solution feed rate and, in extreme cases, a patient's blood could back-flow into the tubing or reservoir. This "blood back-up" scenario might not be detected or avoided in the prior art pumps because the pumps operate independently of the fluid pressure at the point it enters the patient. As mentioned above, those prior art devices do not respond to large discrepancies between the pressure of the fluid in the bag and its pressure at the point it enters the patient, even though such pressure may vary significantly as the relative height of the pump to the patient changes.

It is an object of the present invention to provide a system and a method to control the infusion of intravenous fluid into a patient from an infusion pump.

It is another object of the present invention to provide a system and a method to control the infusion of intravenous fluid into a patient from an infusion pump independent of pump height relative to the patient and without making contact with the intravenous fluid.

It is a further object of the present invention to provide a system and a method to control the infusion of intravenous fluids into a patient independent of the height of the pump relative to the patient by applying external pressure to the flexible, disposable tube which supplies the fluid from the pump to the patient.

It is yet another object of the present invention to provide a safety feature and method to make infusion pumps less susceptible to undesirable "free-flow" and "blood back-flow" situations.

It is yet a further object of the present invention to provide a system and method to increase the safety of infusion pumps designed for use by patients outside the close supervision provided in a hospital.

Other and additional objects are apparent from the following discussion of the invention and its preferred embodiment.

SUMMARY OF THE INVENTION

The present inventive system and method reduces or eliminates undesirable gravitational, inertial and hydraulic effects caused by varying the height of a pump relative to the infusion fluid receiving patient. The system and method uses a shut-off valve on the flexible, disposable tube communicating between the pump and the patient. The valve operates on an on/off basis; closed by the valve's mechanical pinching action, pressing one wall of the tube against the opposing wall, unless the valve is mechanically retracted to allow the tube to open. Because the valve is removable from the disposable tube leading to the patient and never contacts the infusion solution, the valve need not be replaced or sterilized between uses.

The shut-off valve electronically communicates with the pump to determine whether to open or close, depending on the pressure of the fluid within the reservoir. The valve is opened and solution is allowed to flow through the tubing only when the pressure of the fluid in the bag reaches a predetermined minimum value. The valve thereafter closes to prohibit further flow only when the pressure in the bag falls below a certain predetermined, lower value.

The pressure in the reservoir is measured by a sensor located between the plate which pushes against the reservoir and the reservoir itself. The pressure sensor is either an electrical pressure transducer, spring/switch arrangement, or other known means for determining the pressure of the fluid within the reservoir. The pressure transducer determines the internal fluid pressure within the reservoir from a position isolated from contact with the fluid by using the relationship between plate pressure and fluid pressure at points along the path of movement of the plate. The system uses this relationship to calculate the internal reservoir pressure from the plate pressure, plate position and previously determined relationship between those parameters and fluid pressure.

The system controls the opening and closing of the valve at a frequency dependent entirely upon changes in the pressure of the fluid in the reservoir and independent of measurements of other parameters which may affect the fluid flow. The valve stays open for whatever period it takes for a pressure drop to occur in the reservoir from a predetermined minimum "open" value to a lower, predetermined "close" value. The length of time the valve is open and the frequency between openings, i.e., the time for each pressure drop and intervening increase to occur, will depend on the actual rate of fluid flow when the valve is open and the rate the pump is set to operate to increase pressure on the reservoir. The actual rate of pressure increase or decrease in the reservoir when the inventive system and/or method is in use depends on the complex relationship of the height of the pump to the patient, the rate of increase of pressure applied by the pump on the reservoir and other uncontrolled factors.

The present inventive system and method avoids the need to directly measure the rate of flow of the fluid or the height of the pump relative to the patient. Allowing the tube between the reservoir and patient to be open only the length of time it takes for the pressure to drop from a predetermined value to a lower predetermined value automatically adjusts for these factors.

The inventive system and method addresses the principle that a column of fluid in a tube below a reservoir will, under the laws of gravity and capillary action, create a pressure to syphon the entire contents of the reservoir into a patient without positive pressure being applied to the walls of the reservoir. This possibility is prevented by closing the valve unless a certain minimum pressure is present in the bag which results from forces mechanically applied to the reservoir by the pump. Hence, uncontrolled free-flow of fluid into the patient is prevented.

The inventive system and method also provides protection against blood back-flow by taking advantage of the principle that fluid will always flow from the source of greater pressure. If the connection between the reservoir and the patient is closed unless the minimum pressure in the reservoir will overcome the greatest possible back pressure (i.e., when the pump is placed at the entire length of the tube below the patient) positive flow out of the reservoir and into the patient is assured. Setting a minimum pressure in the reservoir which is high enough to overcome the negative pressure of the fluid in the tube before the valve will open protects against undesirable blood back-flow.

When the pump is above the patient, the fluid will be under greater pressure at the point of infusion into the patient than at the pump and will flow faster per time interval into the patient than if the patient and pump were at the same level. Accordingly, when the valve is opened, the pressure in the reservoir will fall faster during this "free flow" scenario than if the pump were at the same height as or lower than the patient. Hence, the valve will be open for a shorter period of time for this situation because it takes a shorter period of time for the pressure in the reservoir to drop to the predetermined shut-off value.

When the valve is closed and the infusion pump is operated to increase the rate of infusion to the patient, the pressure build-up within the reservoir will occur faster, and the predetermined "open" value will be reached more quickly, than it would if the pump was set to infuse at a constant or decreasing rate. Hence, when the pump is set to infuse fluid at an increasing rate, the valve generally will be opened at an increasing rate.

When the pump is below the patient, the same logic applies to assure that the fluid pressures experienced by the patient are maintained within limits. The minimum pressure value to open the valve is set high enough so that adequate pressure exists in the reservoir to obtain positive fluid flow into the patient and prevent any back-flow, even if the pump is as far below the patient as possible. When the pump is below the patient, the rate of flow when the valve is open initially will be slower than when the pump is at the same height as the patient. Accordingly, in this situation, the valve will be open longer (and possibly during the full course of treatment).

DETAILED DESCRIPTION OF THE PREFERRED EMBODIMENT

Figure 7:
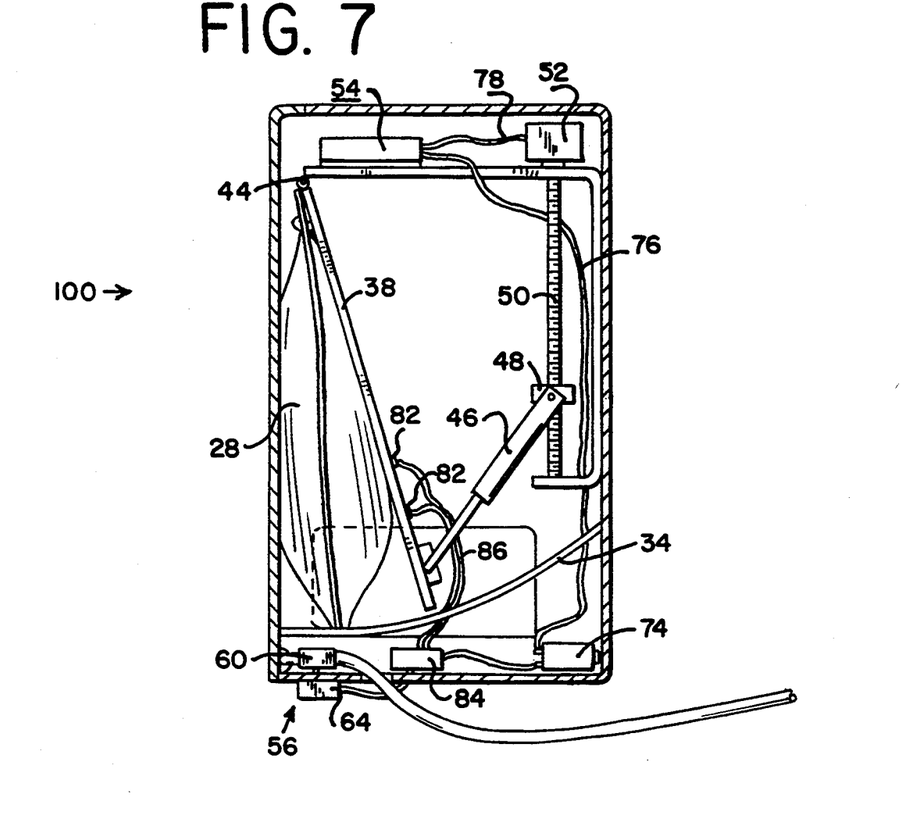
FIG. 7 is a cross-sectional view of an alternative embodiment as it would look at section line 3—3 of FIG. 2.
Figure 8:
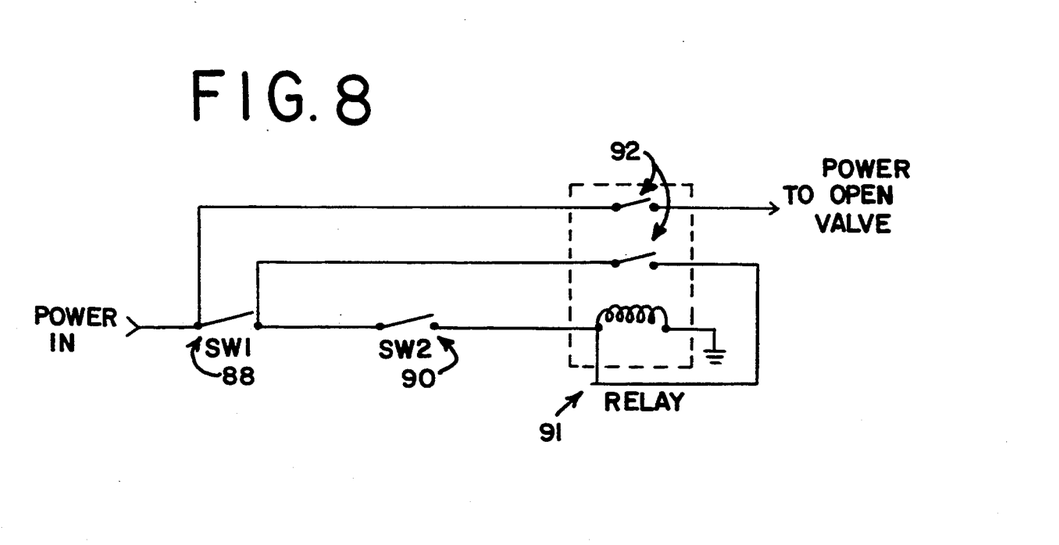
FIG. 8 is a schematic diagram of the switch circuit logic employed by the alternative embodiment.

The preferred embodiment of the present invention in its three liter configuration is depicted in FIGS. 1-6. FIG. 7 shows an alternative embodiment and FIG. 8 shows a circuit diagram relating to an aspect of the alternative embodiment. FIGS. 9-12 show graphic representations of how the inventive valve system which is the subject of this application operates to control fluid flow.

The preferred embodiment is a portable infusion pump 10 for infusing fluids into a patient's vein, stomach, intestine, body cavity or other body lumen or organ. Such fluids could include blood or blood components, drug containing solutions, nutritional fluids, or other medically significant liquids. The pump is self-contained and of a size and weight appropriate for the size of the fluid containing bag to be used in the pump. For a three liter bag, or smaller, the pump will be of a size and weight which is appropriate for carrying on the patient's back, if desired. Shoulder straps 12 are attached to the front of the device (identified as the front to be consistent with the front of the patient when the pump is worn on the patient's back) for convenient carrying by the patient.

Figure 1:
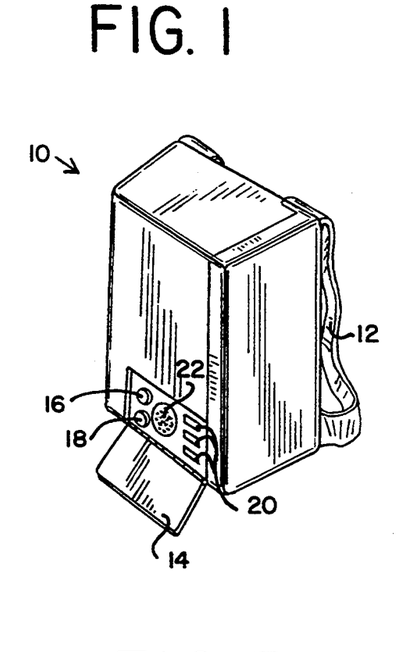
FIG. 1 is a perspective rear view of the preferred embodiment of the present invention.

The rear of the pump contains an access panel 14 which folds down to reveal a series of controls, signal producing lights and a speaker. The controls shown in FIG. 1 are intended to represent generally a control button 16 and control knob 18 and are not intended in any way to limit the number or types of controls which could be accessible behind the access panel 14. The controls 16 and 18 will allow the operator to set the parameters which will guide operation of the pump without requiring the operator to gain access to the interior of the pump 10.

The display windows 20 are visible when the panel 14 is opened and will indicate whether the power of the unit is on, whether the unit is presently administering fluid to the patient and other information about the status of the pump. A speaker 22 to allow an alarm sound is also visible behind the panel 14 and is audible even when the panel is closed. The alarm will be sounded when the pump malfunctions or some parameter monitored by the pump, such as reservoir fluid pressure, departs by a predetermined amount from the normal conditions.

Figure 2:
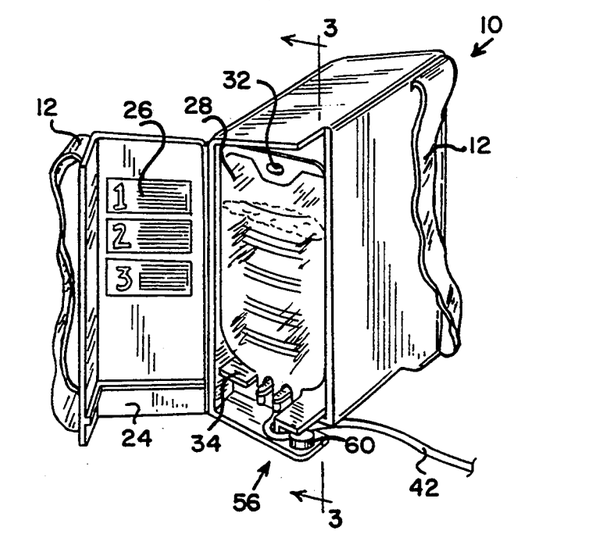
FIG. 2 is a perspective front view of the preferred embodiment of the present invention, shown with access door open and tube attached.

The interior of the pump 10 is accessible by opening pump door 24 which has on its inside surface a series of instructions 26 for loading and operating the pump, making important information about the pump permanently and easily available to the patient or non-patient operator. A standard intravenous bag 28 hangs with ports 30 downward from a hook 32 opposite of the door. The lowest portion of bag 28 contacts a bag support wall 34 which has slots 36 at its edge nearest the door 24 to allow the ports 30 to pass downwardly through the wall 34.

Figure 3:
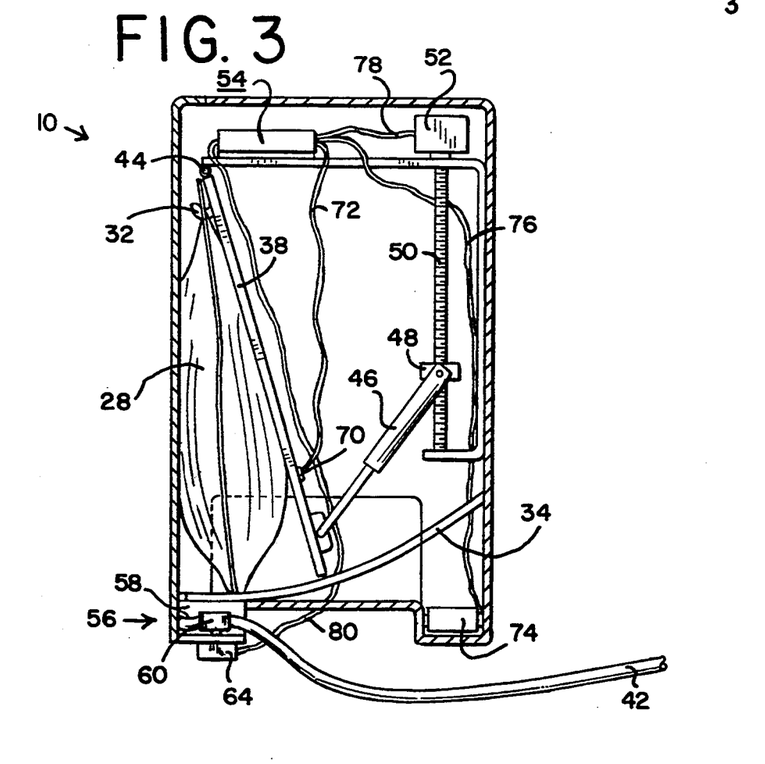
FIG. 3 is a cross-sectional view of the preferred embodiment taken at section line 3—3 in FIG. 2.

As shown in FIG. 3, the fluid containing bag 28 is squeezed by moveable wall 38 to put pressure on the fluid in the bag 28 to flow out middle port 40 and through flexible disposable tube 42 attached to the port 40. The moveable wall 38 is pivotally attached to the pump 10 at pivot 44, oriented in an "inverted V" with the pump door 24 against which the bag 28 is pushed. The wall 38 is moved toward, and pressure is maintained against the bag 28 by push arm 46 which is pivotally connected to both the wall 38 and screw collar 48 which in-turn travels downwardly on screw shaft 50. Screw shaft 50 is rotated to move the screw collar by screw shaft motor 52 which is actuated by controller 54. The arrangement of push arm 46, screw shaft 50 and motor 52 and the mechanical advantages it provides and other details of the pump is described in detail in allowed U.S. patent application Ser. No. 969,981, filed Nov. 2, 1992, incorporated by reference herein.

Figure 4:
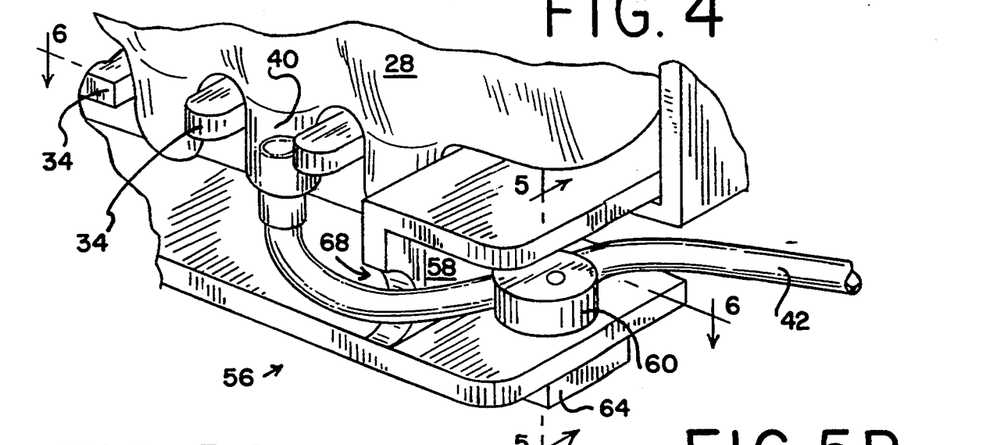
FIG. 4 is an enlarged view of the valve of the preferred embodiment.
Figure 5A:
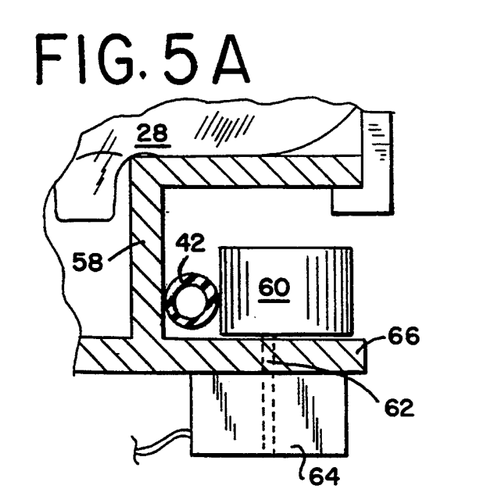
FIG. 5A is a cross-sectional view of the valve of the preferred embodiment taken at section line 5—5 in FIG. 4, shown with valve in the open position.
Figure 5B:
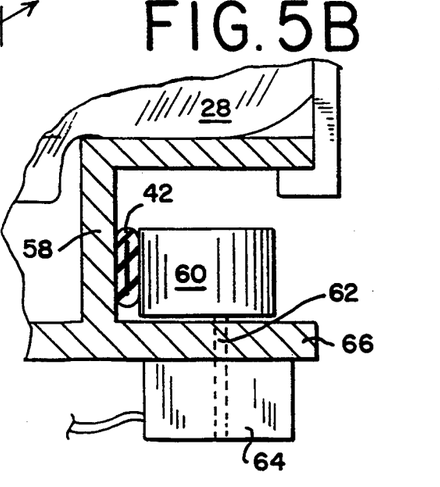
FIG. 5B is a cross-sectional view of the valve of the preferred embodiment taken at section line 5—5 in FIG. 4, shown with valve in the closed position.
Figure 6:
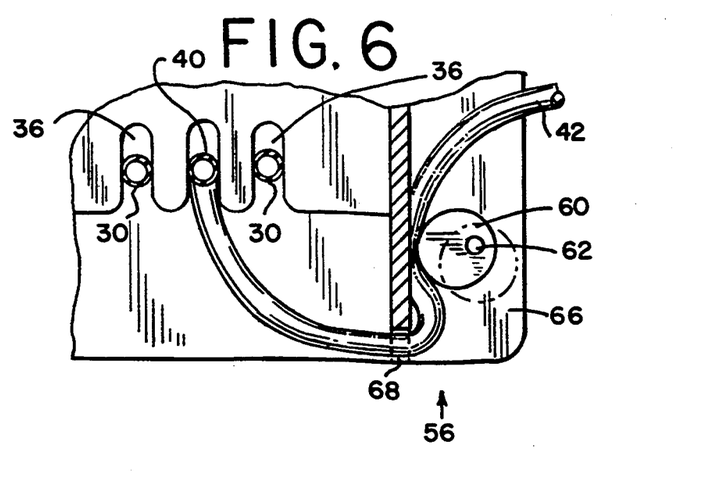
FIG. 6 is a cross-sectional view of the valve of the preferred embodiment taken at section line 6—6 in FIG. 4.

Flow of fluid out of the bag 28 through tube 42 is controlled by valve assembly 56, shown in detail in FIGS. 4-6. The flexible disposable tube 42 is attached at one end to the middle port 40 of the bag 28 and is threaded between stationary valve plate 58 and valve eccentric 60. The eccentric is cylindrical with flat bottom and top, and is mounted on a rotating shaft 62 at a point off-center such that rotation of the shaft 62 and attached eccentric 60 will pinch the tube 42 against the plate 58. In this manner, actuation of the valve motor 64 will rotate the eccentric from a position allowing the tube to be completely open, as shown in FIG. 5A, to a position completely closing the tube, as shown in FIG. 5B.

The entire valve assembly 56 resides just under the shoulder of the bag 28, defined by a top wall formed from an extension of the bag support wall 34, a side wall comprised of the stationary valve plate 58, and an attached horizontal bottom wall 66, through which the shaft 62 passes between the eccentric 60 and the motor 64. A semi-circular aperture 68 is provided in the plate 58 to allow the tube 42 to pass through and between the plate 58 and the eccentric 60.

Aperture 68 provides the only exit route for a tube 42 connected to the bag 28 when the pump door 24 is closed. The pump will not operate unless the door 24 is completely closed and the tubing 42 will block closure of the door 24 unless it is fed through the aperture 68. Once the tube 42 is fed through the aperture 68 and into the valve assembly 56, it passes between the eccentric 60 and the valve plate 58 where it is closed by the valve assembly 56 until the pump is operating and the requisite minimum pressure in the bag 28 is achieved. Accordingly, the aperture 68 acts as a safety feature to avoid misfeeding of the tube from the pump to the patient without passing through the valve.

Although the valve assembly 56 is shown in the preferred embodiment as attached to and part of the pump, it alternatively could be a self contained, independent unit without departing from the general concepts of the present invention.

Referring now specifically to FIG. 3, the preferred embodiment contains a pressure sensing transducer 70 which is mounted to the moveable wall 38 and passes therethrough to contact the outside of the reservoir bag 28. The transducer 70 converts the pressure of the bag 28 against the moveable wall 38 to electrical impulses which are electronically communicated to controller 54 through wire 72. The transducer 70 may be a "Force Sensing Resistor" available from Interlink Electronics, located in Carpinteria, Calif., or other pressure sensing transducer known in the art such as a solid state sensor, mechanical sensor, capacitive sensor or resistance type sensor.

One of the advantages provided by the present invention is that it operates to control the flow of the infusion fluid without contacting it, thereby avoiding contamination of the fluid or otherwise compromising the sterility of the system. This advantage is accomplished in part by the ability of the internal reservoir pressure to be measured without contact with the interior of the reservoir 28. Because the pressure of the bag 28 against the moveable wall 38 is not the same as the internal pressure of the fluid in the bag, a calculation or approximation in the controller 54 must be made.

The pressure of the fluid in the bag can be determined by the pressure sensed by the transducer 70 from two pieces of information; the relationship of the pressure of the fluid to the pressure sensed by the transducer at any given position of the wall 38 relative to the bag 28, and, because the surface area of contact between the bag 28 and the wall 38 changes as the wall 38 moves, the particular position of the wall 38 at the time the pressure is sensed. The relationship of transducer sensed pressure to fluid pressure over the entire course of wall 38 movement can be empirically determined and entered into the memory of the controller 54. The actual transducer sensed pressure is of course determined by the transducer 70 during operation of the pump. The controller 54 knows the actual position of the wall 38 when the transducer pressure is measured because its memory keeps track of the number of turns of the screw shaft motor 52.

The controller 54 is a solid state computer processing unit such as those known in the art. It operates from power supplied by battery pack 74 which contains disposable batteries or a rechargeable D.C. power unit.

The battery pack 74 communicates with the controller through wire 76. Alternatively, the pump can be powered by household or hospital electric current supplied to the pump by an electrical cord as is known in the art.

The controller 54 communicates with screw shaft motor 52 through wire 78 to send impulses to direct it to rotate. As mentioned above, the controller keeps track of the absolute number of turns it has directed the screw shaft to turn in order to know in its memory the position of the moveable wall 38. Alternatively, the position of the moveable wall 38 could be determined by magnetic position sensors or other means known in the art.

The controller 54 also controls the actuation of the valve motor 64 between the open position and the closed position through impulses communicated through wire 80. The valve motor is biased to maintain the eccentric in the closed position, pinching the tube shut, if no impulse is received from the controller 54. This assures that flow of liquid through the tube 42 is restricted if the power source for the pump is disrupted. The movement of the eccentric between the open and closed position is determined by the controller based on a number of predetermined and programmed parameters, as will be discussed below.

An alternative embodiment 100 of the present invention is shown in FIGS. 7 and 8. This embodiment utilizes a simpler spring biased switch arrangement in place of the pressure sensing transducer 70 discussed above. Specifically, the pressure sensing transducer 70 which communicates with the preferred embodiment 10 is replaced by a series of spring biased switches 82 which communicates with the valve motor 64 without first communicating with the controller 54. The switches are mounted on the moveable wall 38 to contact the outside of the bag 28 to determine the pressure at each switch point. FIG. 7 shows two switches 82 as representative of a series of switches; the invention contemplates that a larger number, perhaps dozens of switches may be needed to obtain the desired information of bag pressure and to accurately estimate the fluid pressure within the bag 28.

The switches 82 communicate with a relay 84 over wire 86. The relay 84 further communicates with battery pack 74 and valve motor 64 and determines whether to instruct the valve motor 64 to open or close the eccentric 60 against the tube 42 according to the circuitry shown in FIG. 8.

As representative of more sophisticated systems with dozens or hundreds of switches, switch 1, shown schematically as 88, and switch 2, shown schematically as 90, complete a circuit to open the valve assembly 56 only when both switches are tripped, i.e., when the pressure reaches a predetermined minimum level. For example, switch 1 (88) closes at 2.0 psi pressure of the fluid in the bag 28 (actual transducer pressure may be different) and switch 2 (90) closes at 2.1 psi; both switches (88, 90) will be closed and the relay 91 energized (closing both relay switches 92) only when the fluid pressure detected in the bag reaches 2.1. This completes the circuit to energize and open the valve assembly 56.

The circuit will act to close the valve assembly 56 when the pressure drops below a certain predetermined pressure. The relay switches 92 are normally open and will close only when the relay is energized or continues to receive current. After the relay 91 is energized, and the valve is open, the opening of switch 2 (90) when the pressure drops below 2.1 psi will not disrupt power to maintain the valve open. However, when the pressure drops below 2.0 psi, switch 1 (88) will open and the power to the relay 91 will be discontinued, opening relay switches 92 and discontinuing power to the valve. Hence, after the circuit is energized at 2.1 psi pressure to open the valve, it will stay energized, and the valve will stay open, until the pressure falls below 2.0 psi.

FIGS. 9-12 disclose representative patterns of pressure of the fluid in the reservoir 28 when either the preferred or alternative embodiments are operated. It has been determined that the tube 42 should be closed when the pressure in the bag is above 2.5 psi or below 1.8 psi and the preferred embodiment contains an alarm which will sound if the pressure rises above 2.5 or drops below 1.8. Preferably, the valve system will operate to open only when the fluid pressure in the bag 28 reaches 2.1 and will remain open until the pressure drops to 2.0 psi.

Figure 9:
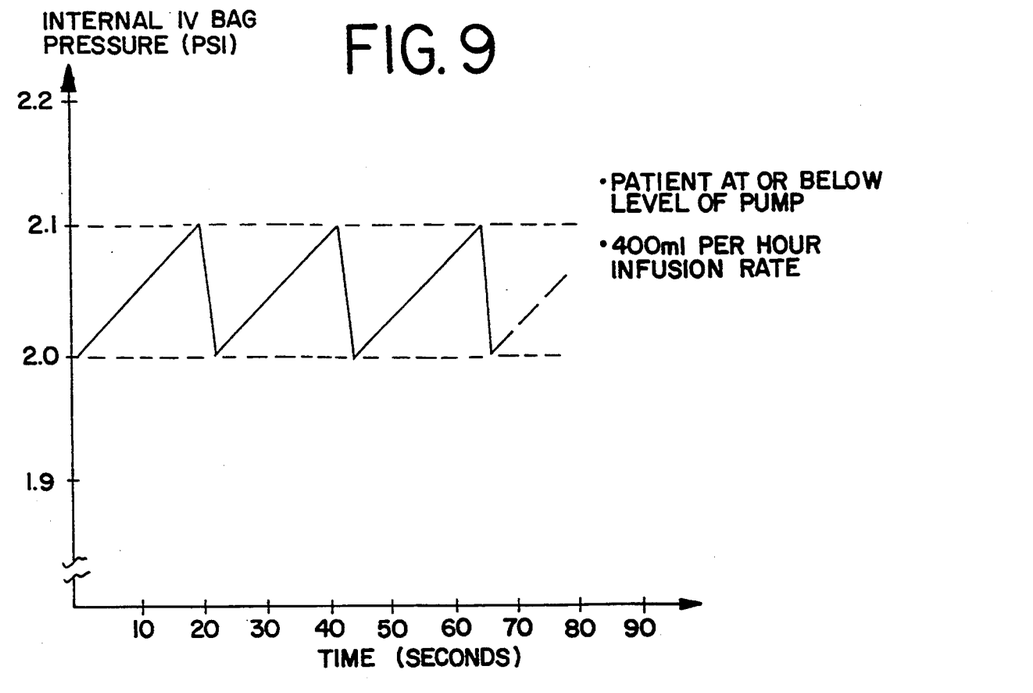
FIG. 9 is a graphic representation of internal fluid pressure within the reservoir over time when the preferred embodiment of the invention is employed for a patient at or below the level of the pump and the desired pump delivery rate is a constant 400 milliliters per hour.

FIG. 9 shows the periodic rising and falling of the fluid pressure in the bag 28 when the minimum open value is set at 2.1 psi, the close value is set at 2.0 psi, the infusion rate is set at 400 milliliters per hour, and the patient is at or below the pump. The valve does not open until the pressure produced in the bag (as a result of the moveable wall 38 pushing against the bag) builds to 2.1 psi, the predetermined minimum value for opening the tube 42. Once the tube 42 is opened, the fluid flows through the tube to the patient and the pressure drops, as shown in the first downward line in the graph.

When the pressure reaches 2.0 psi, the predetermined value for closing the valve, the valve is closed and the pressure in the bag 28 begins to rise until it reaches the 2.1 psi "open" value again. At this point, the valve re-opens, and the pressure in the bag once again drops. This periodic opening and closing is repeated in this scenario of constant infusion rate approximately every 20 seconds. It is known from testing that, for the 2.1 psi and 2.0 psi open and close values, about two to four milliliters of fluid will be expelled from the bag each time the valve is opened.

Figure 10:
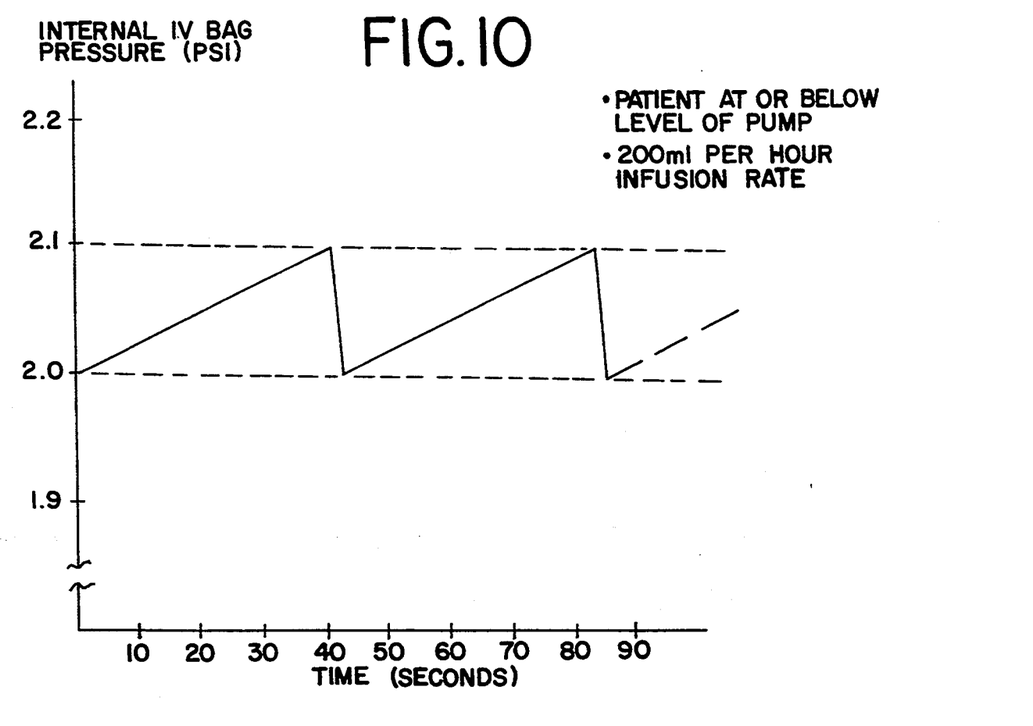
FIG. 10 is a graphic representation of internal fluid pressure within the reservoir over time when the preferred embodiment of the invention is employed for a patient at or below the level of the pump and the desired pump delivery rate is a constant 200 milliliters per hour.
Figure 11:
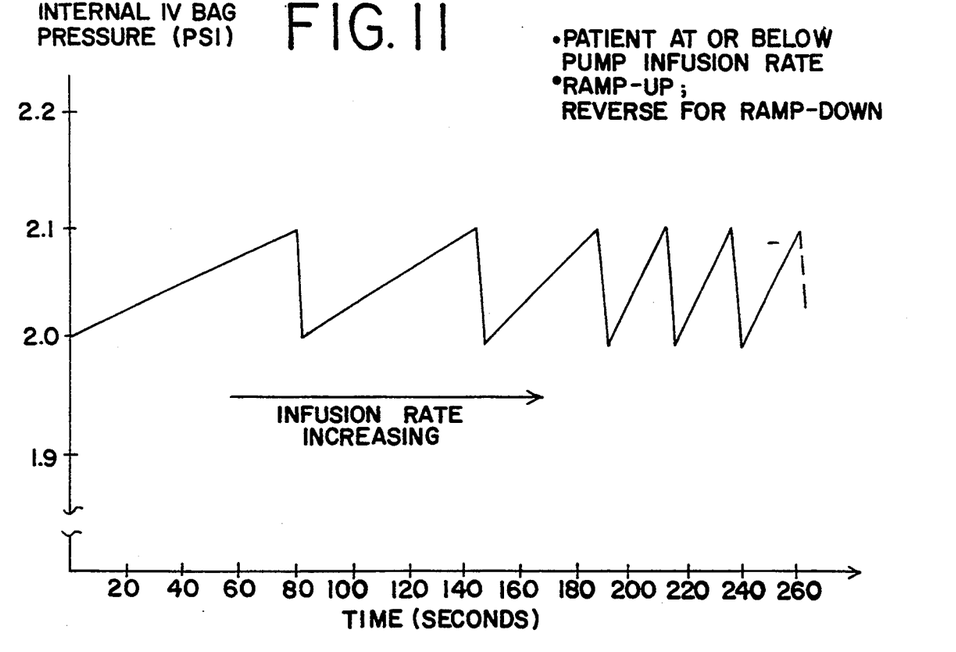
FIG. 11 is a graphic representation of internal fluid pressure within the reservoir over time when the preferred embodiment of the invention is employed for a patient at or below the level of the pump and the desired pump delivery rate is increasing.

FIG. 10 shows the same scenario only this time with a slower, 200 milliliters per hour infusion rate. Again, a pattern is created of periodic opening and closing as the pressure in the bag 28 rises and falls. Because the pump will be set to deliver only half the rate of fluid in FIG. 10 as that delivered for the system represented in FIG. 9, the build up of pressure by operation of the moveable wall 38 will occur over twice as long a period, about 40 seconds instead of about 20 seconds, and the valve is opened only half as often. The inventive valve system accomplishes this without measuring any system parameter except the pressure of the fluid in the bag 28.

FIG. 11 again shows the same scenario, with pump at the same level with or above the patient, but now with an increasing infusion rate over time. Here, the moveable wall 38 will produce the increase in pressure in the bag 28 in increasingly shorter time periods when the valve is closed. Accordingly, the valve assembly is opened more and more frequently as time goes on.

Figure 12:
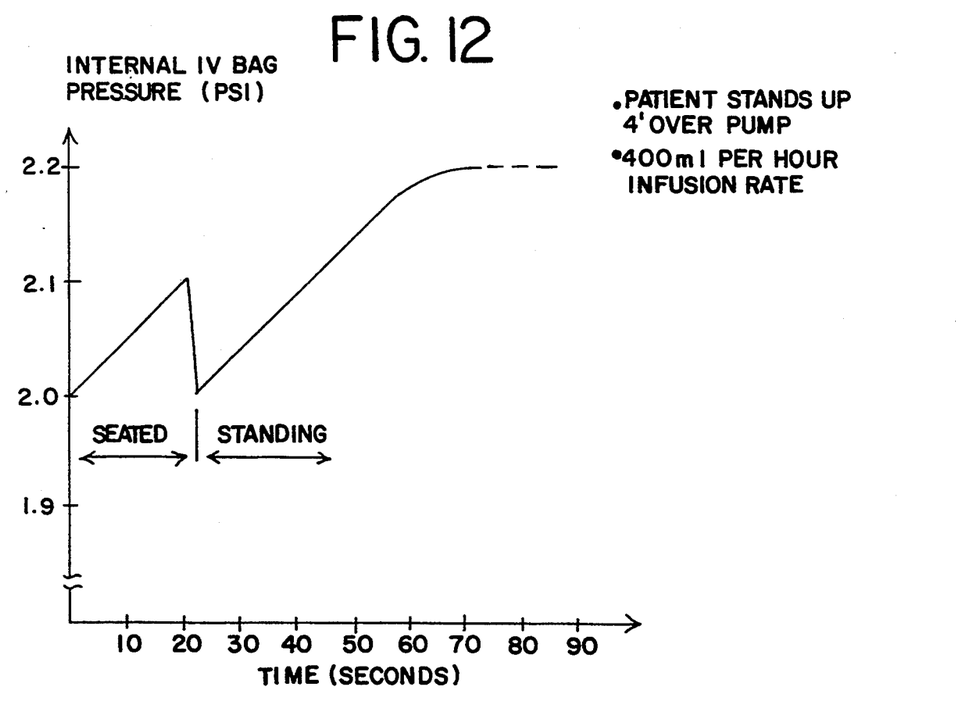
FIG. 12 is a graphic representation of internal fluid pressure within the reservoir over time when the preferred embodiment of the invention is employed for a patient who moves from a position level with the pump to a position four feet over the level of the pump.

FIG. 12 presents a graph showing one of the advantages of the inventive valve system. The desired infusion rate is set for a constant 400 milliliters per hour, and the patient is initially at or below the pump, but suddenly stands up to be four feet above the pump. Without the inventive valve system, the risk of back flow of blood or unacceptably large loss of flow of the infusion fluid would occur. Back flow is avoided because the level of fluid pressure in the reservoir is high enough to overcome typical back flow forces before the valve is opened.

When the patient stands up, for example, the pressure does not drop for a long period of time at the point the tube enters the patient because the valve stays open while the fluid in the reservoir continues to build to overcome the force of gravity on the fluid in the tube 42 above the bag 28. Hence, even though the valve assembly is open, the pressure is allowed to climb to an appropriate higher pressure in the bag 28, shown as about 2.2 psi, to provide the added pressure needed to avoid back flow and to continue to infuse fluid into the patient.

The present invention contemplates a new method as well as a new valve system. The method comprises the steps of allowing fluid flow through the tube 42 only when the pressure in the reservoir is at or above a first predetermined value, and stopping the fluid flow when the pressure drops to a second, lower predetermined level. The preferred first and second predetermined values are 2.1 psi and 2.0 psi respectively, but could alternatively be different without departing from the general concepts of the inventive method.

As was previously mentioned, one of the advantages of the present invention is that it does not prejudice the sterility of the fluid or require the use of expensive or unique disposables. The infusion bag may be a standard disposable infusion bag well known in the art and does not need to be specially designed for this system. The pressure of the fluid in the bag 28 is determined without either contacting the fluid or requiring a special bag 28.

Similarly, the tube used in the contemplated preferred and alternative embodiments is a standard, in-line, intravenous administration set commonly available to doctors and hospitals. The valve acts to pinch the tube shut from the outside to close the tube 42, and does not contact the fluid flowing through the tube 42. Sterility of the system is preserved between uses merely by disposing of the tube 42 after each administration. No specially designed tube is needed for the system.

From the above description it will be apparent that there is provided a system and a method having desirable advantages, but which are susceptible to modification in form, method, operation, detail, construction and arrangement without departing from the principles involved or sacrificing any of its advantages.

It is to be understood that the invention is not limited to the specific features shown, but that the means, method, and construction herein disclosed comprise the preferred form of several modes of putting the invention into effect, and the invention is therefore claimed in any of its forms or modifications within the legitimate and valid scope of the appended claims.

What is claimed is:

1. A system to control fluid flow from a fluid-containing reservoir in an infusion pump to a patient through a tube, the system comprising:
   pressure sensing means for sensing the pressure of the fluid within the reservoir;
   valve means associated with the tube for reversibly restricting fluid flow through the tube, the valve means communicating with the pressure sensing means and being actuated between an open position and a closed position as a result of changes in the pressure of the fluid within the reservoir as detected by the sensing means.

2. The invention of claim 1, further comprising control means communicating between the pressure sensing means and the valve means for actuating the valve means between the open position and the closed position in response to changes in the pressure of the fluid in the reservoir.

3. The invention of claim 1 or claim 2, wherein the valve means is actuated to an open position from a closed position when the pressure of the fluid within the reservoir increases to above a first predetermined value and from an open position to a closed position when the pressure falls below a second predetermined value.

4. The invention of claim 3, wherein the first predetermined value is higher than the second predetermined value.

5. The invention of claim 4 wherein the first predetermined value is about 2.1 psi.

6. The invention of claim 5, wherein the second predetermined value is about 2.0 psi.

7. The invention of claim 1, further comprising alarm means communicating with the pressure sensing means, the alarm means capable of emitting a humanly detectable signal, the alarm being actuated when the pressure of the fluid in the reservoir exceeds a maximum value or falls below a minimum value.

8. The invention of claim 7, wherein the maximum value is about 2.5 psi and the minimum value is about 1.8 psi.

9. The invention of claim 1, wherein the valve means is isolated from the interior of the tube and the fluid which flows therethrough, and wherein the valve means presses one side of the tube against the opposing side of the tube when the valve means is actuated to the closed position.

10. The invention of claim 1 or claim 9, wherein the tube is a flexible disposable tube communicating between the pump and the patient.

11. The invention of claim 2, wherein the pressure sensing means comprises a pressure sensing transducer and wherein the control means comprises logic circuitry.

12. The invention of claim 1, wherein the pressure sensing means comprises a series of spring biased switches.

13. The invention of claim 1, wherein the pressure sensing means is isolated from the fluid in the reservoir.

14. The invention of claim 2, wherein the control means includes means for calculating the pressure of the fluid in the reservoir from a measurement of external pressure and a previously determined relationship of external pressure to fluid pressure.

15. The invention of claim 1, wherein the valve means is biased to be oriented in the closed position unless it is actuated to be in the open position.

16. A system for control of fluid flow from a fluid-containing reservoir in an infusion pump to a patient through a flexible tube, the system comprising:
   a pressure sensing transducer associated with the pump for detecting changes in the pressure of the fluid in the reservoir;
   a valve associated with the tube, the valve having an open position allowing fluid flow through the tube and a closed position prohibiting fluid flow, the valve being isolated from the interior of the tube and the fluid which flows therethrough; and,
   logic circuitry communicating between the transducer and the valve for actuating the valve between open and closed positions in response to changes in the pressure of the fluid within the reservoir, and wherein the logic circuitry actuates the valve to an open position from a closed position when the pressure of the fluid within the reservoir increases to above a first predetermined value and from an open position to a closed position when the pressure falls below a second predetermined value.

17. The invention of claim 16, wherein the first predetermined value is higher than the second predetermined value.

18. The invention of claim 17 wherein the first predetermined value is about 2.1 psi.

19. The invention of claim 17, wherein the second predetermined value is about 2.0 psi.

20. The invention of claim 16, wherein the pressure sensing transducer is isolated from the fluid in the reservoir.

21. The invention of claim 16, wherein the logic circuitry includes means for calculating the pressure of the fluid in the reservoir from a measurement of external pressure and a previously determined relationship of external pressure to fluid pressure.

22. The invention of claim 16, wherein the valve is biased to be oriented in the closed position unless it is actuated to be in the open position.

* * * * *